(12) United States Patent
Wendland et al.

(10) Patent No.: US 11,446,445 B2
(45) Date of Patent: *Sep. 20, 2022

(54) DRUG DELIVERY DEVICE

(71) Applicant: Sanofi-Aventis Deutschland GMBH, Frankfurt am Main (DE)

(72) Inventors: Stefan Wendland, Frankfurt am Main (DE); Anke Liewald, Frankfurt am Main (DE); Frank Richter, Frankfurt am Main (DE); Caroline Stephan, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 645 days.

This patent is subject to a terminal disclaimer.

(21) Appl. No.: 16/395,943

(22) Filed: Apr. 26, 2019

(65) Prior Publication Data
US 2019/0247581 A1    Aug. 15, 2019

Related U.S. Application Data

(63) Continuation of application No. 14/397,186, filed as application No. PCT/EP2013/058837 on Apr. 29, 2013, now Pat. No. 10,293,114.

(30) Foreign Application Priority Data

May 4, 2012    (EP) ..................... 12166720

(51) Int. Cl.
*A61M 5/315*    (2006.01)
*A61M 5/31*    (2006.01)
(Continued)

(52) U.S. Cl.
CPC ........ *A61M 5/3157* (2013.01); *A61M 5/3135* (2013.01); *A61M 5/326* (2013.01);
(Continued)

(58) Field of Classification Search
CPC .............. A61M 5/3157; A61M 5/3135; A61M 5/3257; A61M 5/326; A61M 5/502;
(Continued)

(56) References Cited

U.S. PATENT DOCUMENTS 533,575 A    2/1895    Wilkens
5,226,895 A    7/1993    Harris
(Continued)

FOREIGN PATENT DOCUMENTS

CN    1378468    11/2002
CN    1420794    5/2003
(Continued)

OTHER PUBLICATIONS

Communication from the European Patent Office regarding European Patent Application No. 12166720.8 dated Nov. 7, 2012.
(Continued)

*Primary Examiner* — Lauren P Farrar
*Assistant Examiner* — Hamza A Darb
(74) *Attorney, Agent, or Firm* — Fish & Richardson P.C.

(57) ABSTRACT

The invention relates to a drug delivery device comprising: a syringe with a body from which a needle extends and an inner sheath; a piston rod comprising a piston and an actuation head, a support sheath for holding the body. It is envisaged that the support sheath and the actuation head comprise corresponding indicators.

22 Claims, 9 Drawing Sheets

(51) Int. Cl.
*A61M 5/32* (2006.01)
*A61M 5/50* (2006.01)

(52) U.S. Cl.
CPC ........... *A61M 5/3257* (2013.01); *A61M 5/502* (2013.01); *A61M 2005/3264* (2013.01); *A61M 2205/581* (2013.01); *A61M 2205/582* (2013.01); *A61M 2205/584* (2013.01)

(58) Field of Classification Search
CPC .... A61M 2005/3264; A61M 2205/581; A61M 2205/582; A61M 2205/584; A61M 5/315; A61M 5/31501
See application file for complete search history.

(56) References Cited

U.S. PATENT DOCUMENTS

| | | | |
|---|---|---|---|
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,480,387 A | 1/1996 | Gabriel et al. | |
| 5,505,704 A | 4/1996 | Pawelka et al. | |
| 5,582,598 A | 12/1996 | Chanoch | |
| 5,613,952 A * | 3/1997 | Pressly, Sr. | A61M 5/3234 604/110 |
| 5,626,566 A | 5/1997 | Petersen et al. | |
| 5,674,204 A | 10/1997 | Chanoch | |
| 5,688,251 A | 11/1997 | Chanoch | |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,096,010 A | 8/2000 | Walters et al. | |
| 6,186,980 B1 | 2/2001 | Brunel | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,899,698 B2 | 5/2005 | Sams | |
| 6,936,032 B1 | 8/2005 | Bush, Jr. et al. | |
| 7,118,552 B2 | 10/2006 | Shaw et al. | |
| 7,241,278 B2 | 7/2007 | Moller | |
| 8,603,043 B2 | 12/2013 | Chevalier | |
| 8,628,499 B2 | 1/2014 | Peruzzo | |
| 9,555,196 B2 | 1/2017 | Chevalier | |
| 10,293,114 B2 * | 5/2019 | Wendland | A61M 5/3157 |
| 2002/0052578 A1 | 5/2002 | Moller | |
| 2002/0120235 A1 | 8/2002 | Enggaard | |
| 2002/0193746 A1 | 12/2002 | Chevallier | |
| 2003/0050609 A1 | 3/2003 | Sams | |
| 2004/0059299 A1 | 3/2004 | Moller | |
| 2004/0064106 A1 | 4/2004 | Pressly, Sr. et al. | |
| 2004/0210199 A1 | 10/2004 | Atterbury et al. | |
| 2004/0267207 A1 | 12/2004 | Veasey et al. | |
| 2005/0113764 A1 | 5/2005 | Watkins | |
| 2005/0113765 A1 | 5/2005 | Veasey et al. | |
| 2005/0148943 A1 * | 7/2005 | Chevalier | A61M 5/326 604/198 |
| 2006/0153693 A1 | 7/2006 | Fiechter et al. | |
| 2009/0177156 A1 | 7/2009 | MacLean | |
| 2009/0275916 A1 | 11/2009 | Harms et al. | |
| 2010/0324492 A1 * | 12/2010 | Peruzzo | A61M 5/31511 604/198 |

FOREIGN PATENT DOCUMENTS

| | | |
|---|---|---|
| EP | 0937471 | 8/1999 |
| EP | 0937472 | 8/1999 |
| EP | 0937476 | 8/1999 |
| FR | 2881053 | 7/2006 |
| JP | 11-313888 | 11/1999 |
| JP | 2003-511105 | 3/2003 |
| JP | 2003-522609 | 7/2003 |
| JP | 2004-510554 | 4/2004 |
| JP | 2005-516741 | 6/2005 |
| JP | 2011-504128 | 2/2011 |
| WO | WO 96/40326 | 12/1996 |
| WO | WO 99/38554 | 8/1999 |
| WO | WO 01/10484 | 2/2001 |
| WO | WO 01/60435 | 8/2001 |
| WO | WO 2002/030495 | 4/2002 |
| WO | WO 03/068298 | 8/2003 |
| WO | WO 2009/066130 | 5/2009 |
| WO | WO 2010/066592 | 6/2010 |
| WO | WO 2011/121003 | 10/2011 |
| WO | WO 2012/020086 | 2/2012 |

OTHER PUBLICATIONS

English Translation of First Office Action issued in Chinese Patent Application No. 20138002363-2 dated Apr. 29, 2016, 21 pages.
English Translation of Notice of Reasons for Rejection issued in Japanese Patent Application No. 2015-509394 dated Jan. 24, 2017, 14 pages.
English Translation of Notice of Reasons for Rejection issued in Japanese Patent Application No. 2015-509394 dated Sep. 26, 2017, 9 pages.
English Translation of Official Action issued in Russian Patent Application No. 2014148429/14(077887) dated Apr. 26, 2017, 9 pages.
Form PCT/ISAf220, Notification of Transmittal of the International Search Report and the Written Opinion of the International Searching Authority, or the Declaration dated Jul. 16, 2013.
International Preliminary Report on Patentability in Application No. PCT/EP2013/058837, dated Nov. 4, 2014, 7 pages.

* cited by examiner

DRUG DELIVERY DEVICE

CROSS REFERENCE TO RELATED APPLICATIONS

The present application is a continuation of U.S. patent application Ser. No. 14/397,186, filed Oct. 25, 2014, now U.S. Pat. No. 10,293,114 issued on May 21, 2019, which is a U.S. National Phase Application pursuant to 35 U.S.C. § 371 of International Application No. PCT/EP2013/058837 filed Apr. 29, 2013, which claims priority to European Patent Application No. 12166720.8 filed May 4, 2012. The entire disclosure contents of these applications are herewith incorporated by reference into the present application.

FIELD OF INVENTION

The invention relates to a drug delivery device according to the preamble of claim 1.

BACKGROUND

Administering an injection is a process which presents a number of risks and challenges for users and healthcare professionals, both mental and physical.

Drug delivery devices that are capable of delivering medicaments from a medication container typically designed as manual devices or auto-injectors.

In particular, with a manual device the user must provide the mechanical energy to drive the fluid through the needle. This is typically done by an actuation head coupled to a plunger that has to be continuously pressed by the user during the injection. If the user stops pressing the actuation head then the injection will also stop. This means that the user can deliver an underdose if the device is not used properly (i.e. the plunger is not fully pressed to its end position). Some manual devices are triggered when the user pushes the actuation head complete until the end of the drug delivery process. Usually, the trigger force, which has to overcome, is increased compared to the pure injection force of the drug. This increased force is only sensible on the last one to seven millimetres of the complete device stroke. Because this is on the last millimetres of the stroke, the user gets the impression that the drug delivery process is completed, stops pushing and therefore safety mechanisms/devices for covering the needle will not be activated.

SUMMARY

It is an object of the present invention to provide an improved drug delivery device.

The object is achieved by a drug delivery device according to claim 1.

Preferred embodiments of the invention are given in the dependent claims.

A drug delivery device comprises a longitudinal axis; a syringe with a body having an open proximal end and a distal end from which a needle extends and an inner sheath; a piston rod comprising a piston on a distal end and an actuation head on a proximal end, a support sheath for holding the body. The inner sheath is adapted to be movable between a retracted position in which the needle projects beyond a distal end of the inner sheath and an extended position in which the needle is covered by the inner sheath. The support sheath is adapted to hold the body and to hold the inner sheath in the retracted position as well as in the extended position. The piston rod is movable from a first position in which the piston rod is retracted to a second position wherein a drug delivery process is finished. The actuation head is coupled on a proximal end of the piston rod. The support sheath comprises a proximal section, wherein the proximal section of the support sheath and the actuation head comprise corresponding indicators providing a visible feedback when the piston rod is in the second position.

The invention provides a user of the drug delivery device with a visible and/or audible and/or tactile feedback about the current state of a drug delivery process, in particular to inform the user that the dose of drug was fully delivered so the user can remove the drug delivery device from the injection site, whereby safety features of the drug delivery device, e.g. features to cover the needle, can be activated.

In an exemplary embodiment, the corresponding indicators are designed as coloured and/or tactile markings so as to help the user to get a visible and/or tactile feedback about the current state of the drug delivery process.

In an exemplary embodiment, the coloured and/or tactile markings are formed as fragmented markings and/or circumferential markings, whereby the actuation head comprises a number of fragmented markings and at least one circumferential marking and the support sheath comprises at least one circumferential marking. For example, the fragmented markings are designed as printed or moulded arrows and pointed towards the circumferential marking arranged on the actuation head, whereby the circumferential marking is designed as a printed or moulded circumferential line. When the piston rod is pressed down by application of a sufficient force on the actuation head the circumferential markings of the support sheath and the actuation head come together. Alternatively, the actuation head and the support sheath respectively comprise at least one circumferential marking or respectively a number of fragmented markings.

For an alternative or additional tactile feedback, the actuation head and the support sheath comprise corresponding circumferential latching elements, for example the support sheath comprise a circumferential recess that is suitable to receive a circumferential bulging arranged on the actuation head.

In an exemplary embodiment, the support sheath is made from an optically transparent material and the actuation head is made from an optically intransparent coloured material, whereby the colour of the material of the actuation head differs from the colour of the fragmented and/or circumferential markings so that they are clearly visible for a user. In an alternative embodiment, a finger flange part of the syringe may be transparent and a plunger of the syringe may be made from a coloured material, e.g. in a signal colour. This embodiment also allows for indicating the current state of the injection.

In another exemplary embodiment, the coloured markings are formed respectively as a material colouration, whereby the material of the support sheath is designed at least section wise as a coloured translucent material or as an optically intransparent coloured material or as a transparent material, whereby the degree of transparency or colour of the translucent material and/or the intransparent material of the support sheath is substantially equal to the degree of transparency or colour of the material of the actuation head. Advantageously, with the translucent material the design of the drug delivery device looks visually appealing and further enables an optical scanning during the production process.

In another exemplary embodiment the tactile markings may be formed respectively as a surface modification, in particular a grain.

Furthermore, in another exemplary embodiment, the corresponding indicators are designed as positive locking elements, whereby a first locking element is formed by a circumferential end portion of the actuation head extending in a distal direction, and a second positive locking element that is formed by a proximal section of the support sheath extending in a proximal direction.

In an exemplary embodiment, the first locking element comprises an outer circumference smaller than an inner circumference of the second positive locking element, so that the first locking element will join into the support sheath when the plunger rod is pressed down. To give the user a feedback for the end of drug delivery in an easy way, the first locking element comprises a substantially annular portion that extends perpendicular with respect to the longitudinal axis in such a manner, that a circumference of the annular portion is equal or larger than an outer circumference of the second positive locking element. This enables a visible, audible and/or tactile feedback for the user, because the annular portion abuts against the second locking element when drug delivery is finished. For the user it seems that a gap between the actuation head and the support sheath is closed if the stroke is completed. The drug delivery device looks then closed for the user. The locking element may be configured as one or more circumferential segments or a complete circumferential clip geometry.

In an exemplary embodiment the piston rod is movable between a retracted first position prior to drug delivery and a second position after complete drug delivery, wherein in the second position the annular portion either abuts against the second locking element or wherein the annular portion remains axially spaced from the second locking element by a maximal distance of 3 mm, in particular between 0.1 mm and 3 mm.

In an alternatively exemplary embodiment, the first locking element is designed with a double wall, whereby an outer wall comprises an inner circumference larger than the outer circumference of the second positive locking element, whereby an inner wall comprises an outer circumference smaller than the inner circumference of the second positive locking element, and whereby a recess arranged between the outer wall and the inner wall is formed corresponding to the second positive locking element. This enables a visible and tactile feedback for the user, whereby the actuation head completely overlaps the circumferential portion of the support sheath when drug delivery is finished.

To give the user an additional audible feedback, an exemplary embodiment of the invention provides, that an inner surface of the outer wall comprises at least one first latching element that corresponds to a second latching element arranged on an outer surface of the second positive locking element.

In a further exemplary embodiment, the first latching element is designed as a latching nose, whereby the second latching element is designed as a latching recess, and whereby the latching recess is adapted to receive the latching nose at the end of a drug delivery process. With this, the user gets an "audible click" feedback that drug delivery is finished. Moreover, this provides an indication of use as a "lock in" of the actuation head in the support sheath as to prevent reuse.

In an exemplary embodiment, the second positive locking element comprises a number of spring elements suitable for being inactivated to retain the inner sheath in a retracted position inside the support sheath and for being activated to allow the inner sheath to move in the distal direction towards an extended position. In the mind of the invention, the retracted position of the inner sheath is defined as a position, in which the needle is exposed, whereby the extended position of the inner sheath is defined as a position, in which the needle is covered by the inner sheath. Preferably, the spring elements ensure that the inner sheath is controlled in a manner that is reliable and painless for the user.

In an exemplary embodiment, the spring elements are designed as first resilient tongues that are integral with an inner surface of the second positive locking element and suitable for being moved resiliently from an inactive position to an active position, in which they release the inner sheath from the support sheath, whereby the first resilient tongues are urged towards the active position by a distal movement of the actuation head. This embodiment of the invention provides that the user does not need to perform any additional movement at the end of drug delivery to enable the inner sheath to be extended.

In an exemplary embodiment, the first resilient tongues abut against a number of further spring elements arranged on the inner sheath, whereby the further spring elements are designed as second resilient tongues and held within the support sheath in a snap-fastening manner. Advantageously, the inner sheath is thus held in position in an easy and safety way.

In an exemplary embodiment, the second resilient tongues are resiliently moved inside the support sheath when the first resilient tongues are moved towards their active position, whereby the snap-fit connection of the inner sheath and the support sheath releases. This provides that no special precautions need to be taken as to how the fingers are positioned on the support sheath and on the actuation head in order to ensure that the inner sheath will move to extend over the needle.

For holding the drug delivery device comfortably, at least two finger flanges are arranged on the support sheath and extend perpendicular with respect to the longitudinal axis. In an alternative embodiment, one circular finger flange may be arranged. Thereby, the user can handle the device with two fingers positioned against the finger flanges and one thumb on the actuation head for moving the piston rod. In the second position of the piston rod the finger flanges either abut against the first locking element or the finger flanges remain axially spaced from the first locking element by a maximal distance of 3 mm, in particular between 0.1 mm and 3 mm.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 15 shows a part of a sectional view of a drug delivery device with corresponding positive locking elements in the third embodiment, latching elements, and second spring elements, and.

Corresponding parts are marked with the same reference symbols in all figures.

DETAILED DESCRIPTION

Figure 1:
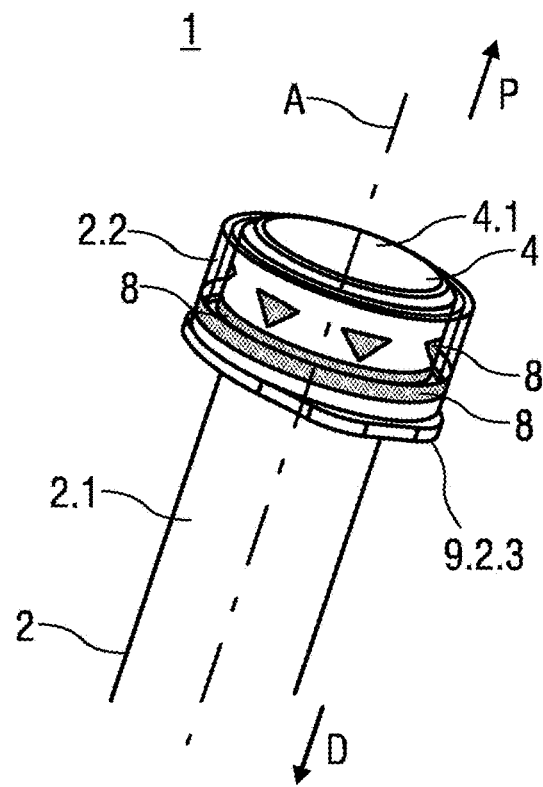
FIG. 1 shows a perspective view of a part of a drug delivery device with a support sheath and an actuation head comprising corresponding coloured markings in a first embodiment.
Figure 2:
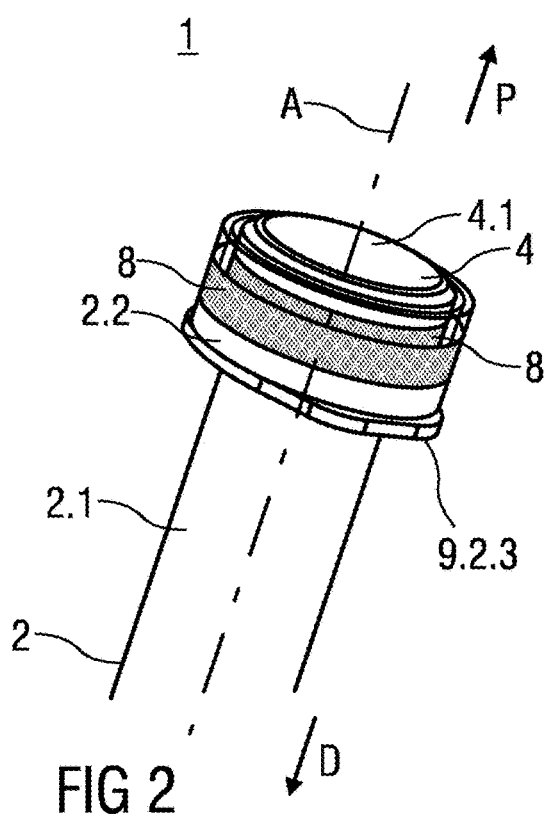
FIG. 2 shows a perspective view of a part of a drug delivery device with a support sheath and an actuation head comprising corresponding coloured markings in a second embodiment.
Figure 3:
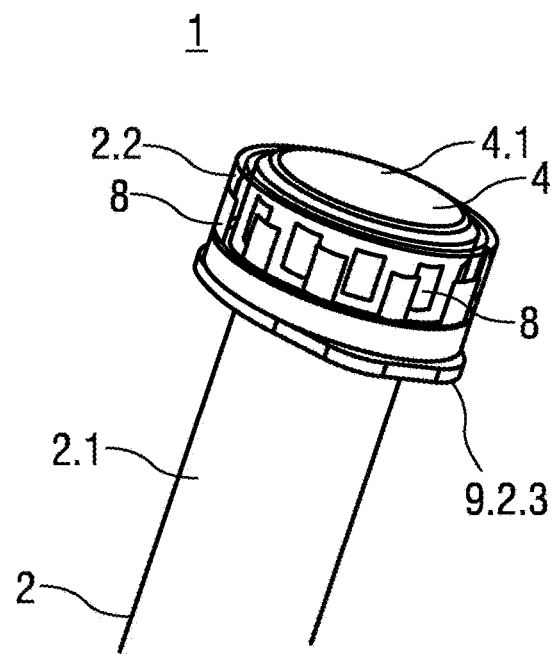
FIG. 3 shows a perspective view of a part of a drug delivery device with a support sheath and an actuation head comprising corresponding coloured markings in a third embodiment.

FIGS. 1 to 3 respectively show a part of a drug delivery device 1 defining a longitudinal axis A. In the following the drug delivery device 1 is considered generally as a device capable of delivering medicaments to a patient in a manual way. The drug delivery device 1 comprises a support sheath 2 and a piston rod 3 that is coupled with an actuation head 4 on a proximal end thereof.

The support sheath 2 is divided into two sections 2.1, 2.2, in particular in a distal section 2.1 designed as a substantially tubular body, and a proximal section 2.2 having a larger diameter than the distal section 2.1.

The proximal section 2.2 can be also described as a circumferential end section of the support sheath 2 that extends parallel to the axis A in a proximal direction P. In the exemplary embodiments of the invention, shown in the FIGS. 1 to 3, an inner periphery of the proximal section 2.2 is suitable to receive a circumferential end portion 4.1 of the actuation head 4 that extends parallel to the axis A in a distal direction D.

Further, the drug delivery device 1 comprises a syringe 5 with a body 5.1 designed as a cartridge respectively pre-filled with a liquid medicament component. The body 5.1 includes an open proximal end and a distal end from which a needle 6 extends. Furthermore, the body 5.1 is held within an inner sheath 7 and is conventionally formed as a substantially tubular body, being made of glass or of plastics material.

The inner sheath 7 is generally in a retracted position inside the support sheath 2 when the piston rod 3 is in a first position, wherein the piston rod 3 is retracted and the drug delivery device 1 is ready for a drug delivery process. The body 5.1 is engaged within the inner sheath 7 and is held relative to the support sheath 2 in such a manner that the needle 6 projects beyond a distal end 2.1 of the support sheath 2 and a distal end 7.1 of the inner sheath 7.

When the piston rod 3 is in a second position, wherein the drug delivery process is finished, i.e. drug is completely delivered; the inner sheath 7 is in an extended position, in which the needle 6 is covered by the inner sheath 7. The body 5.1 is then held within the support sheath 2.

Moreover, the drug delivery device 1 comprises a first spring element 10, preferably designed as a helical spring that is compressed when the inner sheath 7 is retained in the retracted position and that urges the inner sheath 7 to move from the retracted position towards the extended position by relaxing of it. Therefore the first spring element 10 bears against the inner sheath 7 in the distal direction D and against the support sheath 2 in the proximal direction P.

The coupling of the body 5.1 and the inner sheath 7 respective with the support sheath 2 will be described in more detail in the description of FIG. 15.

To provide a user of the drug delivery device 1 with a visible and/or tactile feedback about the current state of the drug delivery process, in particular to inform the user that the dose of drug was fully delivered so the user can remove the drug delivery device 1 from a patient site, the actuation head 4 and the support sheath 2 comprise corresponding coloured and/or tactile markings 8 as indicators.

In a first embodiment shown in FIG. 1, the coloured and/or tactile markings 8 are designed as fragmented and circumferential markings. The actuation head 4 comprises a number of printed or moulded arrows as fragmented markings and one circumferential line as the circumferential marking. The support sheath 2 comprises one circumferential line as circumferential marking.

In a second embodiment shown in FIG. 2, the coloured and/or tactile markings 8 are designed respectively as printed or moulded circumferential lines. In a third embodiment illustrated in FIG. 3, the coloured and/or tactile markings 8 are designed respectively as fragmented lines in the form of a number of printed or moulded squares.

When the piston rod 3 is pressed down by application of a sufficient force on a bearing surface 4.2 of the actuation head 4 the coloured and/or tactile markings 8 of the support sheath 2 and the actuation head 4 come together. Pressing down the piston rod 3 means that it is moved from the first position towards the second position.

For an alternative or additional tactile feedback, the actuation head 4 and the support sheath 2 comprise corresponding circumferential latching elements (not shown). In an example, the support sheath 2 comprises a circumferential recess that is suitable to receive a circumferential bulging arranged on the actuation head 4.

In a further exemplary embodiment of the invention the support sheath 2 is made from an optically transparent material, whereby the actuation head 4 is made from an optically intransparent coloured material. Preferably, the colour of the material of the actuation head 4 differs from the colour of the coloured and/or tactile markings 8 so that they are clearly visible for the user. For example, the material of the actuation head 4 comprises is designed with a green colour and the circumferential and/or fragmented markings include a blue colour.

It goes without saying that the coloured and/or tactile markings 8 described in the above embodiments can be designed as any other geometric form suitable to give a user a clearly visible feedback.

In another embodiment of the invention (not shown in any of the FIGS. 1 to 15), the material of the support sheath 2 is designed at least section wise as a coloured translucent material or as an optically intransparent coloured material. Preferably, a colour of the translucent material and/or the intransparent material of the support sheath 2 is substantially equal to the colour of the material of the actuation head 4.

Figure 4:
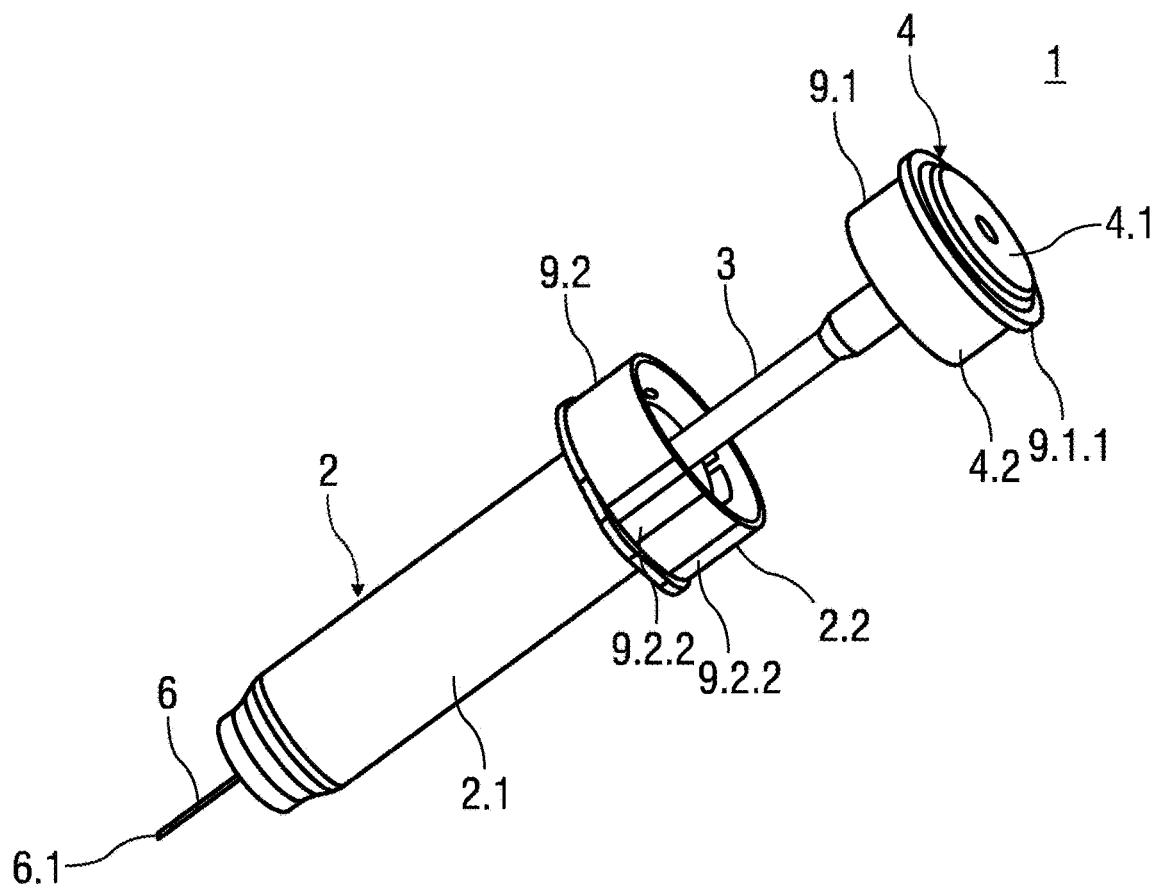
FIG. 4 shows a perspective view of the drug delivery device with a support sheath and a piston rod coupled to an actuation head comprising corresponding positive locking elements in a first embodiment, whereby the piston rod is in a first position.
Figure 5:
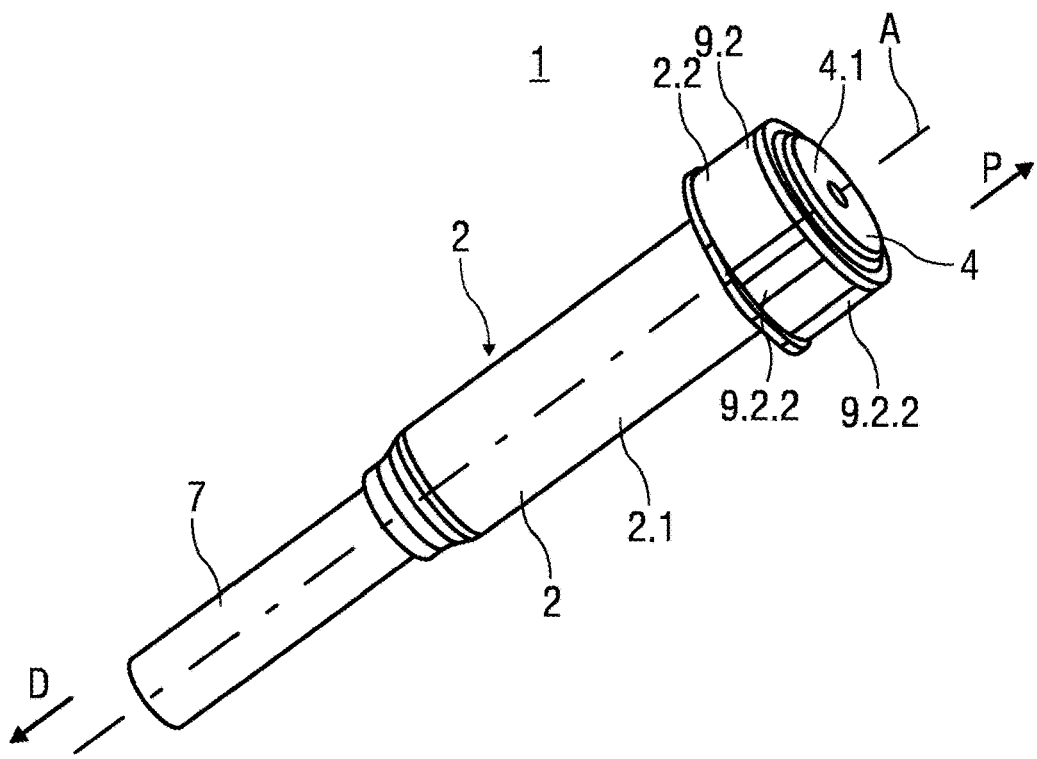
FIG. 5 shows a perspective view of the drug delivery device according to FIG. 4, whereby the piston rod is in a second position
Figure 6:
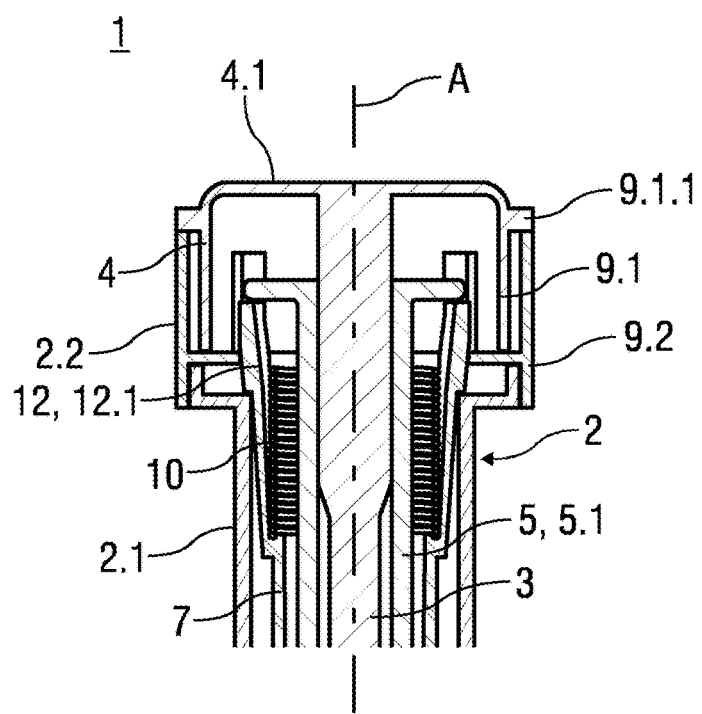
FIG. 6 shows a part of a sectional view of the drug delivery device according to FIG. 5.

The FIGS. 4 to 15 show the drug delivery device 1 with corresponding positive locking elements 9.1, 9.2 in different embodiments as indicators. The FIGS. 4 to 6 show the drug delivery device 1 with the positive locking elements 9.1, 9.2 in a first embodiment.

A first locking element 9.1 is formed by the circumferential end portion 4.1 of the actuation head 4; a second positive locking element 9.2 is formed by the proximal section 2.2 of the support sheath 2.

Figure 7:
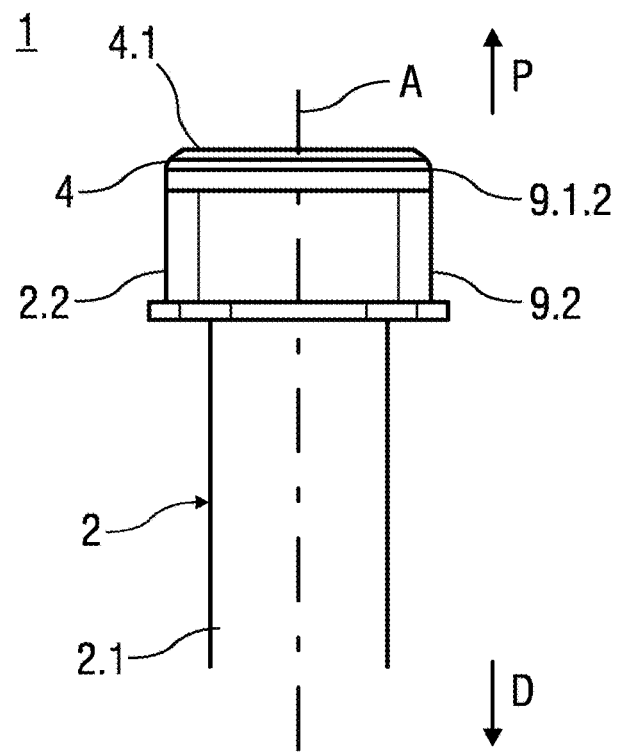
FIG. 7 shows a side view of a drug delivery device with corresponding positive locking elements in a second embodiment.

According to the first embodiment, the first locking element 9.1 comprises an outer circumference smaller than an inner circumference of the second positive locking element 9.2, so that the first locking element 9.1 will join into the second positive locking element 9.2 if the piston rod 3 is moved from the first position, illustrated in FIG. 4, to the second position, illustrated in the FIGS. 5 to 7.

Further, the first locking element 9.1 comprises a substantially annular portion 9.1.1, e.g. a ring, which is arranged proximally and extends perpendicular with respect to the axis A.

A circumference of the annular portion 9.1.1 is equal or larger than an outer circumference of the second positive locking element 9.2. Likewise, the circumference of the annular portion 9.1.1 may be smaller than the outer circumference but greater than the inner circumference of the second positive locking element 9.2. The annular portion 9.1.1 is preferably integral with the actuation head 4 to enable effective costs and maintain regarding to a production process.

The annular portion 9.1.1 abuts against the second locking element 9.2 when the piston rod 3 is in the second position. This enables a visible and tactile feedback for the user when drug is fully delivered. Likewise, a distal edge of the first locking element 9.1 may abut against the second locking element 9.2 when the piston rod 3 is in the second position, while the annular portion 9.1.1 may remain axially spaced from the second locking element 9.2, e.g. by a distance between 0.1 mm and 3 mm. This may lead the user to fully depress the piston rod 3 thereby triggering the inner sheath 7.

Figure 8:
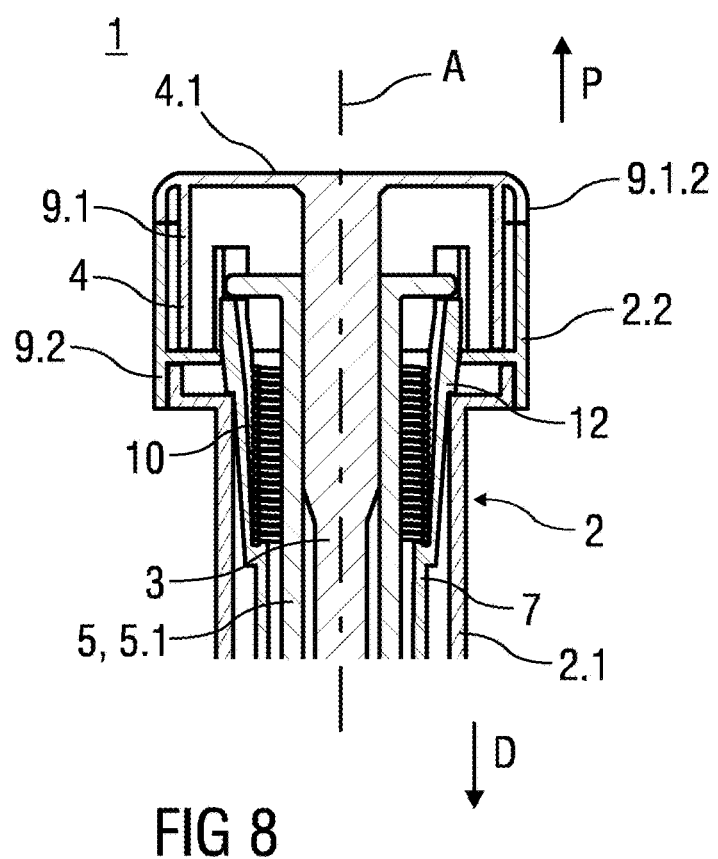
FIG. 8 shows a part of a sectional view of the drug delivery device according to FIG. 7.

The FIGS. 7 and 8 show the positive locking elements 9.1, 9.2 in a second embodiment, wherein the first positive locking element 9.1 comprises a proximal end portion 9.1.2 with a circumference equal to or larger than the inner circumference of the second positive locking element 9.2. The proximal end portion 9.1.2 abuts against the second locking element 9.2 when the piston rod 3 is in the second position equivalent as it is performed by the annular portion 9.1.1.

Figure 9:
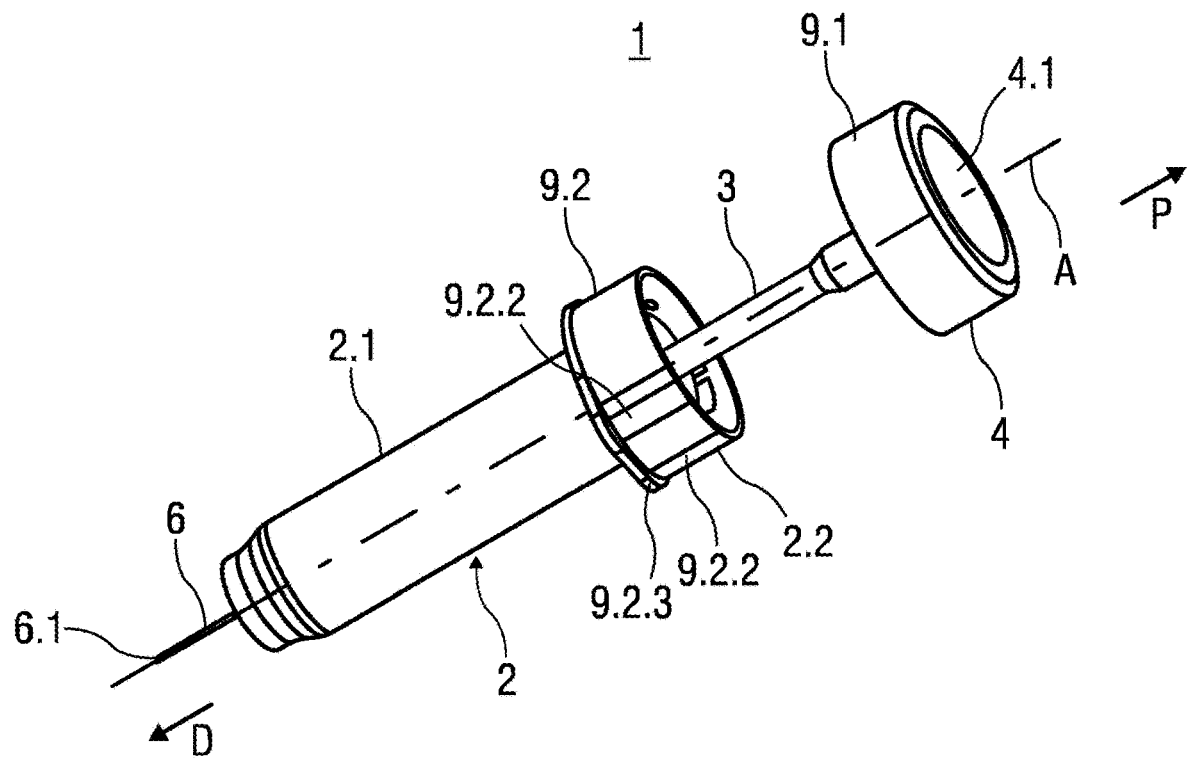
FIG. 9 shows a perspective view of a drug delivery device with corresponding positive locking elements, whereby the piston rod is in a first position.
Figure 10:
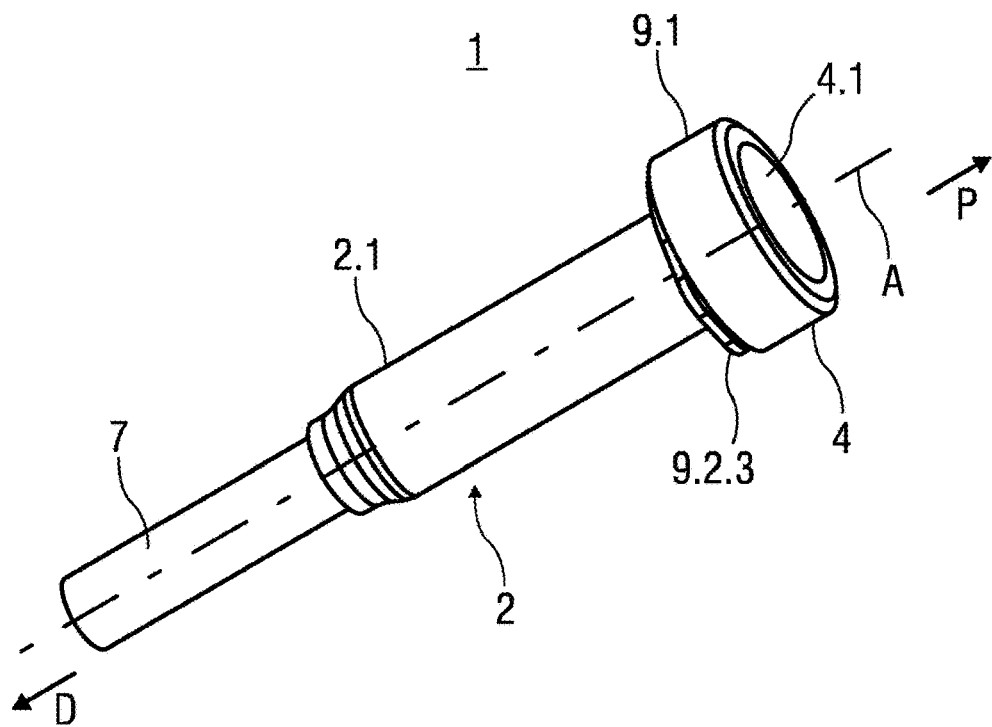
FIG. 10 shows a perspective view of the drug delivery device according to FIG. 9, whereby the piston rod is in a second position.
Figure 11:
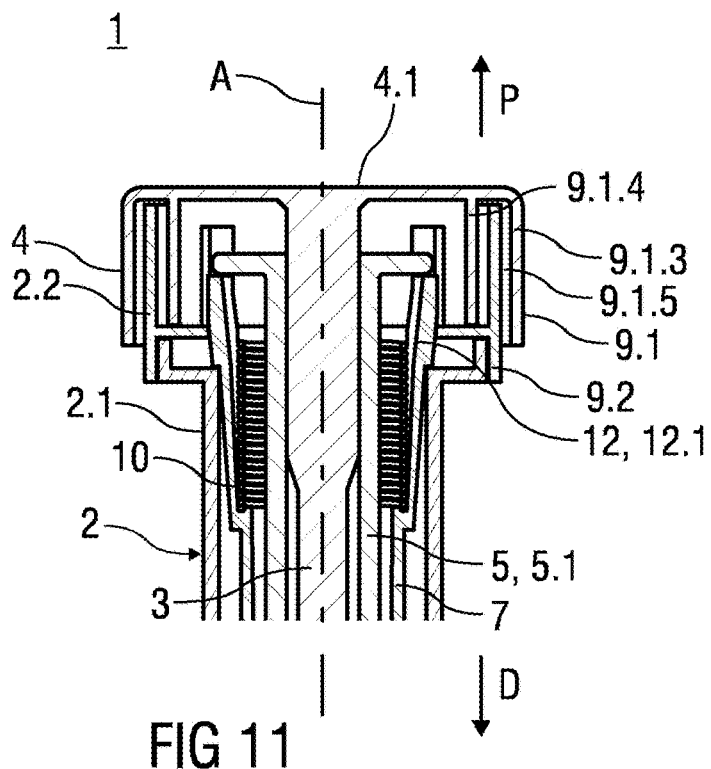
FIG. 11 shows a part of a sectional view of the drug delivery device according to FIG. 10.

The FIGS. 9 to 15 show the drug delivery device 1 with positive locking elements 9.1, 9.2 in a third embodiment, whereby in FIG. 9 the piston rod 3 is retained in the first position and in the FIGS. 10 and 11 the piston rod 3 is retained in the second position.

The first positive locking element 9.1 is designed with a double wall. An outer wall 9.1.3 comprises an inner circumference larger than the outer circumference of the second positive locking element 9.2 and an inner wall 9.1.4 comprises an outer circumference smaller than the inner circumference of the second positive locking element 9.2.

The outer and inner wall 9.1.3, 9.1.4 are spaced apart from each other, hence defining a recess 9.1.5 between, which is formed corresponding to a contour of the second positive locking element 9.2.

When the piston rod 3 is moved from the first position to the second position, the first positive locking element 9.1 moves over the second positive locking element 9.2 in such a manner that the outer wall 9.1.3 moves over the outer surface of the second positive locking element 9.2 and the inner wall 9.1.4 moves over an inside surface of the second positive locking element 9.2.

At the same time the recess 9.1.5 receives the contour of the second positive locking element 9.2. With this, the first positive locking element 9.1 hides the second positive locking element 9.2 when the piston rod 3 is in the second position. The end of drug delivery is then practically indicated when the circumferential end portion 4.1 is moved completely over the proximal section 2.2 of the support sheath 2. This corresponds to a visible feedback.

Figure 12:
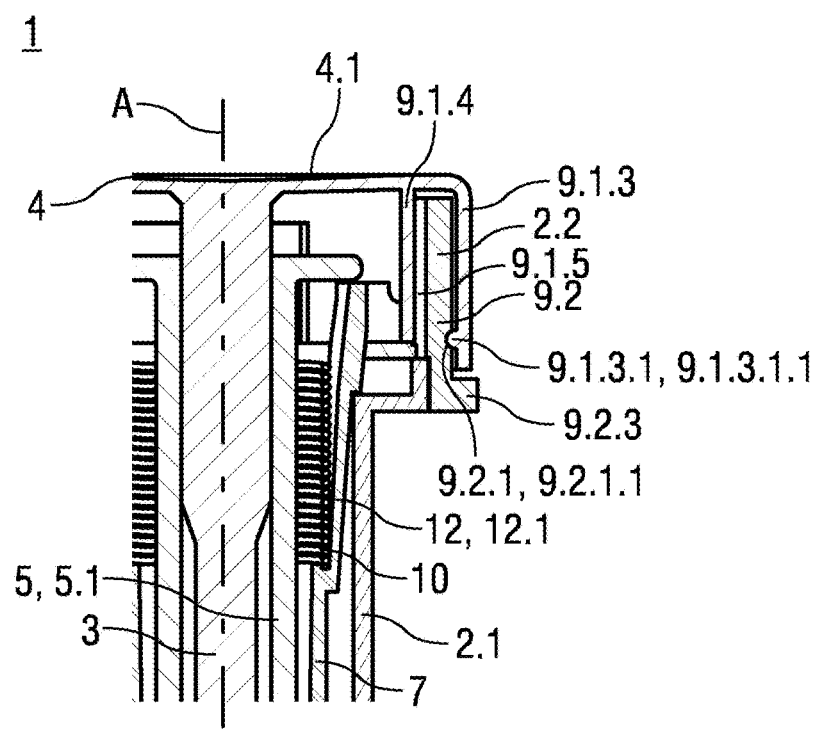
FIG. 12 shows a part of a sectional view of a drug delivery device with corresponding positive elements in the third embodiment and with latching elements.
Figure 13:
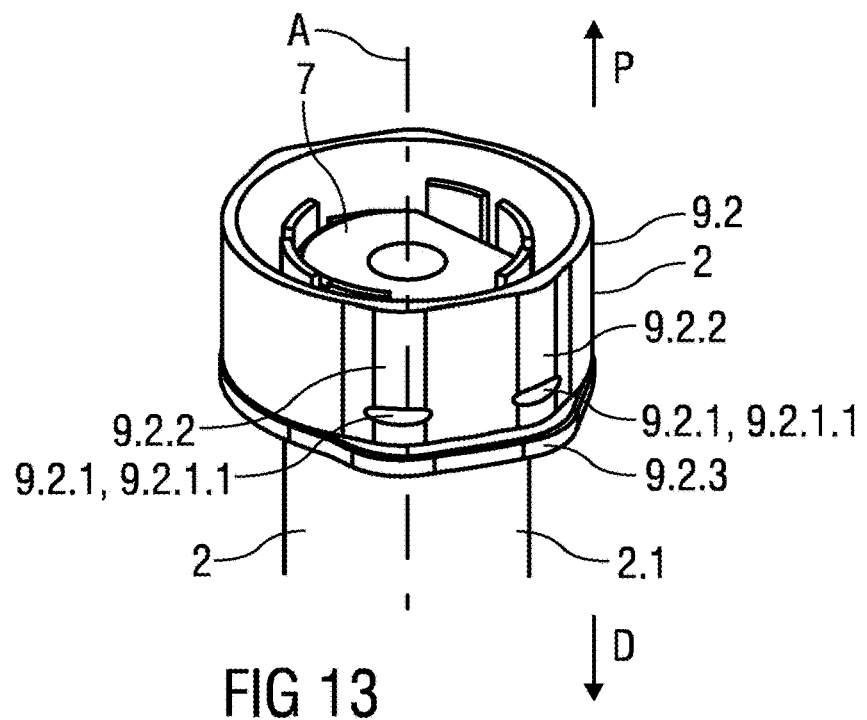
FIG. 13 shows a perspective view of a part of the drug delivery device according to the FIGS. 11 and 12 without actuation head and with an outer contour of a second positive locking element in a first embodiment.

For an additional audible feedback, the FIGS. 12 and 13 show an exemplary embodiment of the invention, wherein an inner surface of the outer wall 9.1.3 comprises a first latching element 9.1.3.1, illustrated in the sectional view of FIG. 12. The first latching element 9.1.3.1 is arranged distally and comprises at least one latching nose 9.1.3.1.1 that is suitable to latch into a corresponding second latching element 9.2.1 arranged distally on an outer surface of the second positive locking element 9.2 and that comprises at least one latching recess 9.2.1.1.

In the terminology of the invention the inner surface of the outer wall 9.1.3 is a surface that is faced towards the inner wall 9.1.4, whereby an inner surface of the inner wall 9.1.4 is a surface faced towards the outer wall 9.1.3.

FIG. 13 illustrates the second positive locking element 9.2 in a perspective view so that two latching recesses 9.2.1.1, spaced apart from each other in a peripheral direction, are visible in more detail. Preferably, the second positive locking element 9.2 comprises two additional latching recesses 9.2.1.1 (not shown) arranged oppositely to the illustrated latching recesses 9.2.1.1. Hence, the outer wall 9.1.3 of the first positive locking element 9.1 comprises four latching noses 9.1.3.1.1.

It goes without saying that the illustrated embodiment in FIG. 13 only shows an exemplary embodiment of the invention. The corresponding latching elements 9.1.3.1, 9.2.1 can comprise a number of latching noses 9.1.3.1.1 respectively latching recesses 9.2.1.1 differing from that what is described above. Further, the first latching element 9.1.3.1 can be designed as a circumferential bulging that latches into the second latching element 9.2.1 designed as a corresponding circumferential recess.

When the piston rod 3 is moved from the first position to the second position and hence the outer wall 9.1.3 moves over the outer surface of the second positive locking element 9.2 the latching noses 9.1.3.1.1 latch into the corresponding latching recesses 9.2.1.1. This provides a feedback in the form of an audible click when drug delivery is finished and an indication of use as a "lock in" of the actuation head 4 in the support sheath 2 as to prevent reuse.

As can be seen further in FIG. 13 (and also in the FIGS. 4, 5 and 9), the second positive locking element 9.2 comprises a number of curvatures 9.2.2 that corresponds to the number of latching recesses 9.2.1.1, whereby the curvatures 9.2.2 are arranged in the area of the latching recesses 9.2.1.1. Preferably, the outer and inner wall 9.1.3, 9.1.4 of the first positive locking element 9.1, in particular the inner surface of the outer wall 9.1.3 and an inner surface of the inner wall 9.1.4, comprise corresponding forms to enable an optimal positive locking fit between the first and second positive locking elements 9.1, 9.2.

Figure 14:
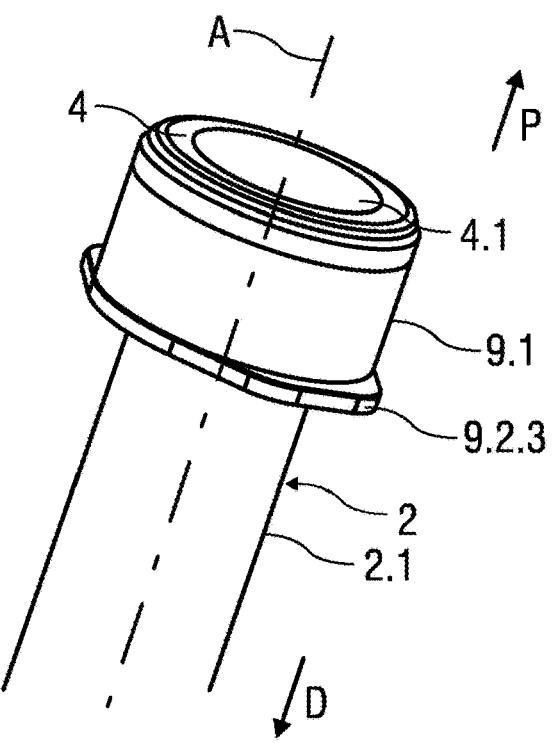
FIG. 14 shows a perspective view of a part of the drug delivery device with a outer contour of the second positive locking element in a second embodiment, whereby the piston rod is in the second position.

FIG. 14 shows an alternative embodiment of the invention, in which the first positive locking element 9.1 comprises a substantially round outer contour. Even it is not illustrated; the second positive locking element 9.2 comprises a corresponding form without the curvatures 9.2.2 shown in FIG. 13. This enables an easy performance of a production process of the drug delivery device 1.

For holding the drug delivery device 1 comfortably, the support sheath 2 comprises two finger flanges 9.2.3 that are illustrated best in FIG. 14. The finger flanges 9.2.3 are arranged distally on the second positive locking element 9.2 and extend perpendicular with respect to the axis A. Thereby, the user can handle the drug delivery device 1 between the index and middle fingers, placing these fingers against the finger flanges 9.2.3 and driving the piston rod 3 by pressing the thumb on the actuation head 4.

In an alternative embodiment a circular finger flange can be arranged.

Figure 15:
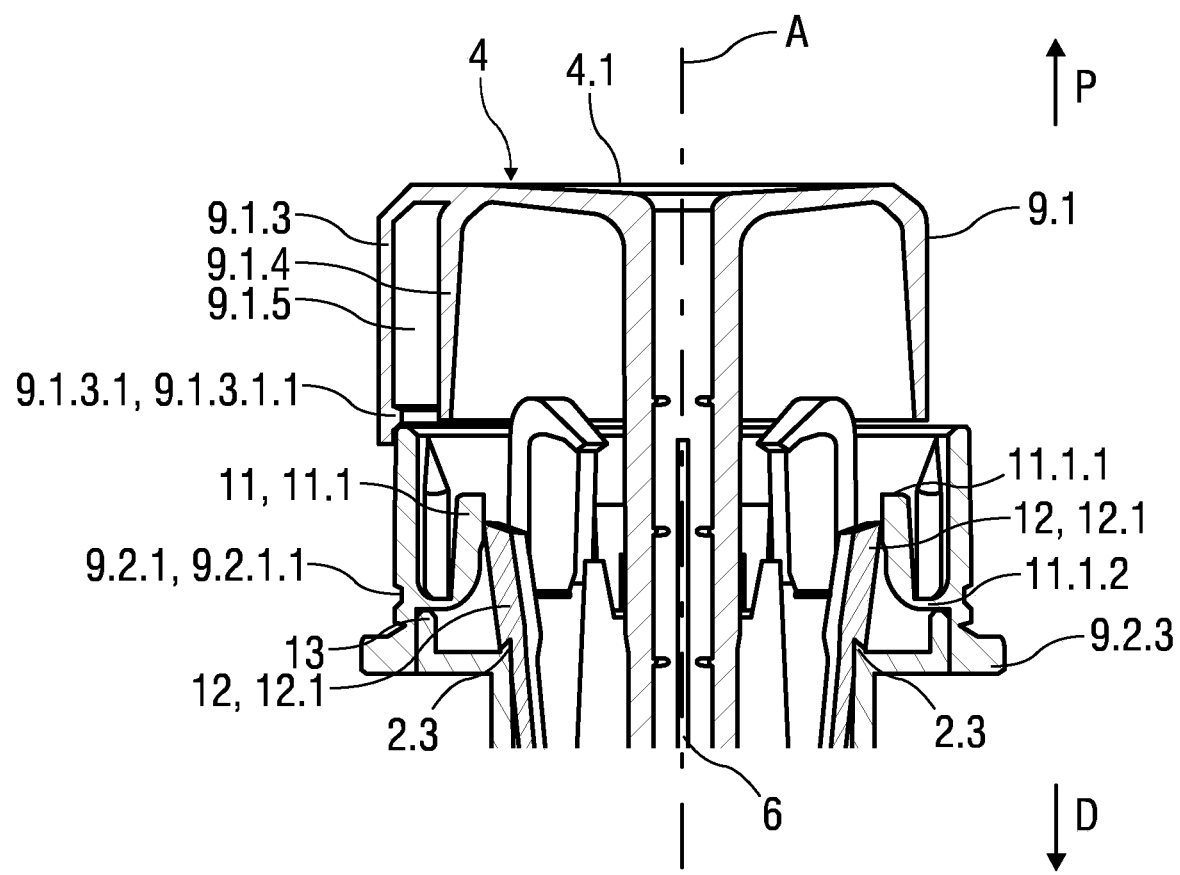

In FIG. 15, a safety mechanism of the drug delivery device 1 is shown in more detail. The safety mechanism enables that the inner sheath 7 is movable from the retracted position to the extended position, in which a distal tip 6.1 of the needle 6 is covered completely by the inner sheath 7.

Therefore, the second positive locking element 9.2 comprises a number of second spring elements 11 designed as resilient tongues, following named as first resilient tongues 11.1, which are integral with an inner surface of the second positive locking element 9.2.

The first resilient tongues 11.1 are directed inwards and build a ramp surface for the first positive locking element 9.1 directed outwards, when the piston rod 3 is moved towards the second position.

A free end 11.1.1 of the first resilient tongues 11.1 abut against third spring elements 12 arranged on the inner sheath 7. The third spring elements 12 are designed as resilient tongues, following named as second resilient tongues 12.1 that tend naturally to spread apart slightly, going away from the axis A. In the example shown, the second resilient tongues 12.1 are integral with the inner sheath 7 and hook onto the support sheath 2, in particular the proximal section 2.2 that comprises therefore corresponding nuts 2.3.

The first resilient tongues 11.1 are suitable for being moved resiliently from an inactive position, in which they abut against the second resilient tongues 12.1 without pre-stressing the second resilient tongues 12.1, to an active position, in which they release the inner sheath 7 from the support sheath 2.

For releasing the inner sheath 7 the second resilient tongues 12.1 are urged by the first resilient tongues 11.1 to move resiliently inside the support sheath 2 by a distal movement of the piston rod 3. In particular, when the inner wall 9.1.4 of the first positive locking element 9.1 has moved over the ramp surface of the first resilient tongues 11.1 it abuts against an end 11.1.2 of the first resilient tongues 11.1 that is arranged on the inner surface of the second positive locking element 9.2.

This abutting causes a resilient movement of the first resilient tongues 11.1 inside the support sheath 2 which in turn causes that the second resilient tongues 12.1 are resiliently moved inside the support sheath 2 releasing the inner sheath 7 from the support sheath 2.

Therefore, the end 11.1.2 of the first resilient tongues 11.1 comprises a material weakness compared to the free end 11.1.1. According to a distal direction D, behind the material weakness a projection 13 is arranged on the second positive locking element 9.2 that projects in the proximal direction P. When the inner wall 9.1.4 abuts against the material weakness and thus the first resilient tongues 11.1 moved resiliently inside the support sheath 2 the material weakness of the first resilient tongues 11.1 abuts against the projection 13. This enables a good "rolling up" of the first resilient tongues 11.1 on the projection 13 so that a risk for damages of the first resilient tongues 11.1 is reduced.

Thus, the actuation head 4 actuated the first resilient tongues 11.1 to release the inner sheath 7. The first spring element 10 thrust the inner sheath 7 forward into the distal direction D so that it projects well beyond the distal section 2.1 of the support sheath 2 over a length suitable for forming a protective shield around the distal tip 6.1 of the needle 6. Thus, a risk for a user to come in contact with the needle 6 after drug delivery is reduced.

Figure 16:
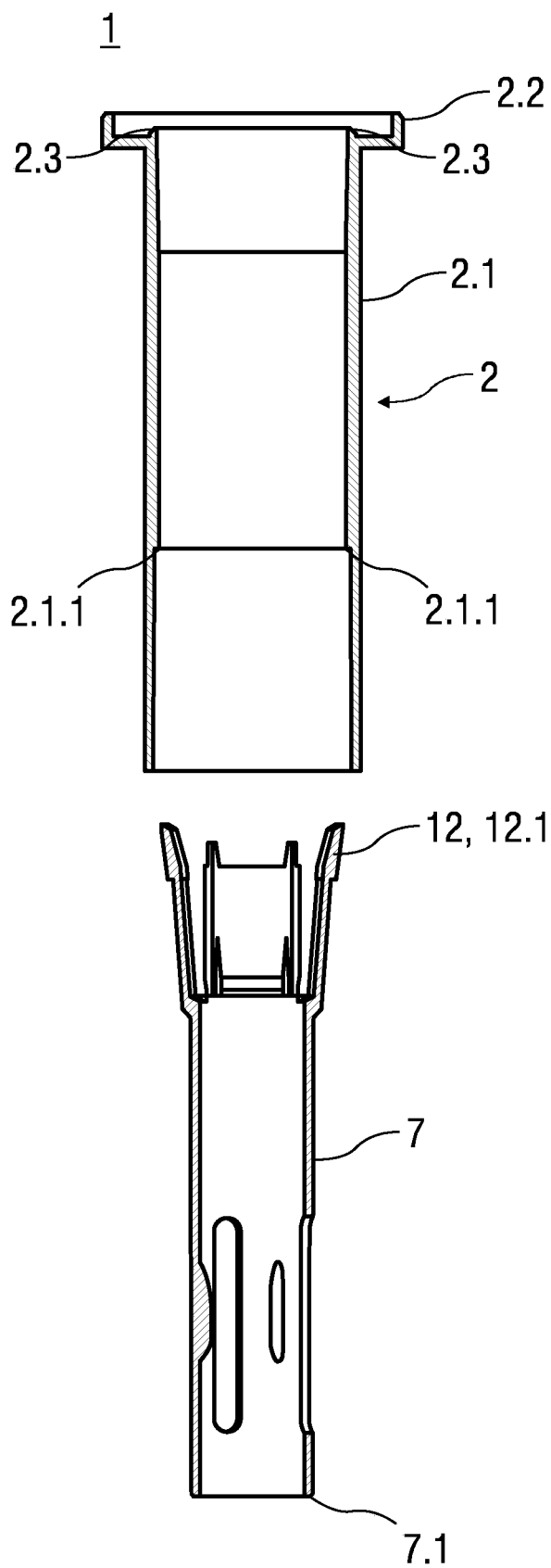
FIG. 16 shows an exploded illustration of a sectional view of a drug delivery device.

The inner sheath 7 is retained in the extended position by coming into abutment against a shoulder 2.1.1 formed into the support sheath 2. Therefore, FIG. 16 shows a drug delivery device 1 in an exploded view. As can be seen a proximal end of the second resilient tongues 12.1 abuts against the shoulder 2.1.1 in the proximal direction P when the inner sheath 7 is retained in the extended position. Thus a proximal movement of the inner sheath 7 is limited when the second resilient tongues 12.1 passes the shoulder 2.1.1. With this the inner sheath 7 is prevented for being retracted into the support sheath 2 and to expose the needle 6. The resilient tongues 12.1 flex outwards against the support sheath 2 so that they always interfere with the shoulder 2.1.1 thus providing reliable safety.

The body 5.1 is held relative to the support sheath 2 in a not shown way by holding elements belonging to the support sheath 2, co-operating with a proximal end of the body 5.1.

The invention claimed is:

1. A drug delivery device comprising:
   a syringe from which a needle extends;
   an inner sheath adapted to be movable between a retracted position in which the needle projects beyond a distal end of the inner sheath and an extended position in which the needle is covered by the inner sheath;
   a support sheath adapted to hold the syringe and to hold the inner sheath in the retracted position as well as in the extended position;
   a piston rod that is movable from a first position in which the piston rod is retracted, to a second position in which a drug delivery process is finished;
   an actuation head that is coupled on a proximal end of the piston rod;
   a first locking element formed by an end portion of the actuation head, the first locking element extending in a distal direction, the first locking element having one or more latching elements arranged on an inner surface of an outer wall of the actuation head; and
   a second locking element formed by a proximal section of the support sheath, the second locking element extending in a proximal direction, the second locking element having a plurality of latching recesses formed on an outer surface of the proximal section of the support sheath, each latching recess being spaced apart from other latching recesses of the plurality of latching recesses,
   wherein the plurality of latching recesses are adapted to receive the one or more latching elements when the piston rod is in the second position.

2. The drug delivery device of claim 1, wherein when the piston rod is in the second position, the latching elements are locked with respect to the latching recesses to prevent a reuse of the drug delivery device.

3. The drug delivery device of claim 1, wherein the second locking element has a first plurality of curved portions, wherein each latching recess of the plurality of latching recesses is formed on a respective curved portion of the first plurality of curved portions.

4. The drug delivery device of claim 3, wherein an outer wall of the second locking element defines the first plurality of curved portions,
wherein an outer wall of the first locking element has an inner circumference larger than an outer circumference of the outer wall of the second locking element, and
wherein the outer wall of the first locking element has a second plurality of curved portions that abut against the first plurality of curved portions when the piston rod is in the second position.

5. The drug delivery device of claim 3, wherein the first locking element comprises an inner wall comprising an outer circumference smaller than an inner circumference of the second locking element, and
wherein the inner wall of the first locking element has a third plurality of curved portions with curvatures that correspond to curvatures of the first plurality of curved portions of the second locking element.

6. The drug delivery device of claim 1, wherein the first locking element has a double wall comprising an inner wall and an outer wall, the inner wall having an outer circumference smaller than an inner circumference of the second locking element, and the outer wall having an inner circumference larger than an outer circumference of the second locking element,
wherein a recess arranged between the outer wall and the inner wall of the first locking element is configured to receive the second locking element when the piston rod is in the second position.

7. The drug delivery device of claim 1, wherein at least two of the latching recesses are arranged opposite one another about a circumference of the second locking element.

8. The drug delivery device of claim 1, wherein the one or more latching elements of the first locking element comprise a plurality of latching noses, each latching nose being received by a respective latching recess when the piston rod is in the second position.

9. The drug delivery device of claim 1, wherein the one or more latching elements of the first locking element comprise a circumferential projection configured to be received by one of the plurality of latching recesses when the piston rod is in the second position.

10. The drug delivery device of claim 1, wherein the actuation head includes one or more fragmented markings that are viewable through the proximal section of the support sheath when the piston rod is in the second position.

11. The drug delivery device of claim 10, wherein the one or more fragmented marking are viewable through a transparent portion of the proximal section of the support sheath when the piston rod is in the second position.

12. The drug delivery device of claim 1, wherein the first locking element has an outer circumference smaller than an inner circumference of the second locking element, and
wherein the first locking element comprises a substantially annular portion that extends perpendicular with respect to a longitudinal axis of the drug delivery device such that a circumference of the annular portion is equal to or larger than an outer circumference of the second locking element.

13. The drug delivery device of claim 12, wherein in the second position the annular portion abuts against the second locking element or the annular portion remains axially spaced from the second locking element by no more than 3 millimeters.

14. The drug delivery device of claim 1, wherein the second locking element comprises a spring element suitable for being deactivated to retain the inner sheath in the retracted position inside the support sheath and for being activated to allow the inner sheath to move in the distal direction into the extended position.

15. The drug delivery device of claim 14, wherein the spring element is designed as a first resilient tongue that is integral with an inner surface of the second locking element.

16. The drug delivery device of claim 15, wherein the first resilient tongue abuts against a second spring element arranged on the inner sheath.

17. The drug delivery device of claim 1, wherein the syringe contains a medicament.

18. The drug delivery device of claim 1, further comprising a flange arranged on the support sheath to extend perpendicular with respect to a longitudinal axis of the drug delivery device,
wherein when the piston rod is in the second position the flange abuts against the first locking element or the flange remains axially spaced from the first locking element by no more than 3 millimeters.

19. The drug delivery device of claim 1, wherein an inner diameter of the outer wall is larger than an outer diameter of the second locking element such that the first locking element at least partially surrounds the second locking element when the piston rod is in the second position.

20. A drug delivery device comprising:
a syringe from which a needle extends;
an inner sheath adapted to be movable between a retracted position in which the needle projects beyond a distal end of the inner sheath and an extended position in which the needle is covered by the inner sheath;
a support sheath adapted to hold the syringe and to hold the inner sheath in the retracted position as well as in the extended position;
a piston rod that is movable from a first position in which the piston rod is retracted, to a second position in which a drug delivery process is finished, and
an actuation head that is coupled on a proximal end of the piston rod;
a first locking element formed by a circumferential end portion of the actuation head, the first locking element extending in a distal direction, the first locking element having one or more latching elements; and
a second locking element formed by a proximal section of the support sheath, the second locking element extending in a proximal direction,
wherein the second locking element has a plurality of latching recesses designed on a plurality of curved portions formed on an outer wall of the second locking element, each latching recess being spaced apart from other latching recesses of the plurality of latching recesses and being formed on a respective curved portion of the plurality of curved portions,
wherein the first locking element has a double wall comprising a first inner wall and a first outer wall, the first inner wall having an outer circumference smaller than an inner circumference of the outer wall of the second locking element, and the first outer wall having an inner circumference larger than an outer circumference of the outer wall of the second locking element, and wherein, when the piston rod is in the second position, a recess arranged between the first outer wall and the first inner wall of the first locking element is configured to receive the outer wall of the second locking element so that each of the latching recesses of the second locking element receives a respective latching element of the first locking element.

21. A method of delivering drug, the method comprising:
moving a piston rod of a drug delivery device from a first position with respect to a syringe to a second position with respect to the syringe to dispense a drug from the syringe through a needle connected to the syringe; and
locking an actuation head coupled on a proximal end of the piston rod when the piston rod reaches the second position, by engaging one or more latching elements arranged on an inner surface of an outer wall of the actuation head with a plurality of latching recesses formed on an outer surface of a support sheath that holds the syringe, and wherein moving the piston rod from the first position to the second position causes an inner sheath of the drug delivery device to move from a retracted position in which the needle projects beyond a distal end of the inner sheath to an extended position in which the needle is covered by the inner sheath.

22. The drug delivery device of claim 20, wherein the one or more latching elements are arranged on an inner surface of the outer wall of the actuation head and the plurality of latching recesses are formed on an outer surface of the proximal section of the support sheath.

* * * * *